US010309938B2

(12) United States Patent
Olovsson

(10) Patent No.: US 10,309,938 B2
(45) Date of Patent: Jun. 4, 2019

(54) ROTARY VALVE

(71) Applicant: GE Healthcare Bio-Sciences AB, Uppsala (SE)

(72) Inventor: Bjorn Olovsson, Uppsala (SE)

(73) Assignee: GE HEALTHCARE BIO-SCIENCES AB, Uppsala (SE)

(*) Notice: Subject to any disclaimer, the term of this patent is extended or adjusted under 35 U.S.C. 154(b) by 264 days.

(21) Appl. No.: 15/103,437

(22) PCT Filed: Dec. 15, 2014

(86) PCT No.: PCT/SE2014/051500
§ 371 (c)(1),
(2) Date: Jun. 10, 2016

(87) PCT Pub. No.: WO2015/094096
PCT Pub. Date: Jun. 25, 2015

(65) Prior Publication Data
US 2016/0305916 A1    Oct. 20, 2016

(30) Foreign Application Priority Data
Dec. 19, 2013  (SE) ........................ 1351526

(51) Int. Cl.
G01N 30/20     (2006.01)
B01D 15/18     (2006.01)
F16K 11/074    (2006.01)

(52) U.S. Cl.
CPC ......... G01N 30/20 (2013.01); B01D 15/1842 (2013.01); F16K 11/0743 (2013.01); B01D 2215/024 (2013.01); G01N 2030/202 (2013.01)

(58) Field of Classification Search
CPC ............. G01N 30/20; G01N 2030/202; B01D 15/1842; B01D 2215/024; F16K 11/0743
See application file for complete search history.

(56) References Cited

U.S. PATENT DOCUMENTS 3,220,164 A   11/1965  Golay et al.
4,614,204 A    9/1986  Dolejs
(Continued)

FOREIGN PATENT DOCUMENTS

WO   2003/026772 A2    4/2003
WO   2003/026772 A3   12/2003
(Continued)

OTHER PUBLICATIONS

International Preliminary Report on Patentability Received for PCT Patent Application No. PCT/SE2014/051500, dated Jun. 21, 2016, 5 pages.
(Continued)

Primary Examiner — David Z Huang
(74) Attorney, Agent, or Firm — Wood IP LLC

(57) ABSTRACT

A rotary valve comprising a stator and a rotor wherein the stator comprises at least three inlet primary connection ports, at least three outlet primary connection ports, at least three inlet secondary connection ports and at least three outlet secondary connection ports, and wherein rotor interconnection paths are arranged to in the different rotor positions interconnect the inlet primary connection ports with the inlet secondary connection ports and the outlet primary connection ports with the outlet secondary connection ports such that all of at least three inlet secondary connection ports can be connected one at the time to each of at least three inlet primary connection port and all of at least three outlet secondary connection ports can be connected one at the time to each of at least three outlet primary connection port by rotating the rotor into the different rotor positions. A chromatography system comprising at least three chromatography columns, a rotary valve connected to the inlets of at least three columns in the system and to at least three inflows and connected to the outlets of at least
(Continued)

three columns in the system and to at least three outflows, and a feed recirculation flow path.

18 Claims, 6 Drawing Sheets

(56) References Cited

U.S. PATENT DOCUMENTS

| | | |
|---|---|---|
| 4,632,149 A | 12/1986 | Oroskar et al. |
| 6,997,213 B1 | 2/2006 | Towler et al. |
| 8,349,175 B1 | 1/2013 | Oroskar |
| 2008/0053543 A1 | 3/2008 | Baier et al. |
| 2011/0067770 A1 | 3/2011 | Pederson et al. |
| 2013/0068977 A1 | 3/2013 | Picha et al. |

FOREIGN PATENT DOCUMENTS

| | | |
|---|---|---|
| WO | 2008/103097 A1 | 8/2008 |
| WO | 2008140374 A1 | 11/2008 |
| WO | 2010056189 A1 | 5/2010 |
| WO | 2014031069 A1 | 2/2014 |
| WO | 2015/094096 A1 | 6/2015 |

OTHER PUBLICATIONS

Extended European Search Report Received for European Patent Application No. 14871221.9, dated May 31, 2017, 8 pages.
International Search Report and Written Opinion Regarding International Application No. PCT/SE2014/051500, dated Mar. 19, 2015, 9 pages.

ROTARY VALVE

CROSS-REFERENCE TO RELATED APPLICATIONS

This application is a filing under 35 U.S.C. 371 of international application number PCT/SE2014/051500, filed Dec. 15, 2014, which claims priority to SE application number 1351526-7, filed Dec. 19, 2013, the entire disclosures of each of which are hereby incorporated by reference.

FIELD OF THE INVENTION

The present invention relates to valves and more specifically to rotary valves.

BACKGROUND

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotor with respect to the stator.

Rotary valves can be designed to withstand high pressures (such as pressures above 25 MPa). They can be made from a range of materials, such as stainless steel, high performance polymeric materials and ceramics.

The number of inlets/outlets as well as the design of grooves in the rotor or the stator reflects the intended use of a specific valve. A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

In chromatography systems for continuous chromatography, such as simulated moving bed systems usually a large number of valves are used for providing feed and buffer to the different columns in the system in correct order. There is a need for better valve arrangements in such systems.

SUMMARY OF THE INVENTION

One object of the invention is to provide a rotary valve that can be used for continuous chromatography.

A further object of the invention is to provide a continuous chromatography system with convenient and effective valve arrangement.

This is achieved in a rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position, wherein the stator comprises at least three inlet primary connection ports, at least three outlet primary connection ports, at least three inlet secondary connection ports and at least three outlet secondary connection ports, and wherein the rotor interconnection paths are arranged to in the different rotor positions interconnect the inlet primary connection ports with the inlet secondary connection ports and the outlet primary connection ports with the outlet secondary connection ports such that all of at least three inlet secondary connection ports can be connected one at the time to each of at least three inlet primary connection port and all of at least three outlet secondary connection ports can be connected one at the time to each of at least three outlet primary connection port by rotating the rotor into the different rotor positions.

It is also achieved in a chromatography system comprising at least three chromatography columns, said system comprising:
  a rotary valve as defined above connected to the inlets of at least three columns in the system and to at least three inflows and connected to the outlets of at least three columns in the system and to at least three outflows, and
  a feed recirculation flow path in which feed recirculation from the outlet of the column presently serving as primary load column in a chromatography process to the inlet of the column presently serving as secondary load column is transferred,
  wherein said feed recirculation flow path transfers the feed recirculation from all the columns in the system serving as load columns and wherein said feed recirculation flow path is connected to the inlets and outlets of the columns through the rotary valve.

Hereby at least three columns and at least three inflows and at least three outflows can be connected to the rotary valve and the rotary valve can connect the inflows and the outflows to any one of the columns. This can be used in a chromatography system. This will provide a flexible rotary valve for use in for example a simulated moving bed chromatography system. Hereby a chromatography system with a rotary valve and feed recirculation can be provided. This will give a system with fewer valves and fewer flow connections compared to traditional simulated moving bed chromatography systems. This will provide a convenient and improved rotary valve and chromatography system.

In one embodiment of the invention the interconnections of the primary connection ports with the secondary connection ports will be shifted according to a simulated moving bed process by rotating the rotor.

In one embodiment of the invention the rotor interconnection paths are partly bending grooves.

In one embodiment of the invention the rotor interconnection paths are arranged to:
  in a first rotor position: a first inlet primary valve orifice C1 is connected to a first inlet secondary valve orifice 95a, a second inlet primary valve orifice C2 is connected to a second inlet secondary valve orifice 95b, a third inlet primary valve orifice C3 is connected to a third inlet secondary valve orifice 95c, a fourth inlet primary valve orifice C4 is connected to a fourth inlet secondary valve orifice 95d, a first outlet primary valve orifice C1' is connected to a first outlet secondary valve orifice 95a', a second outlet primary valve orifice C2' is connected to a second outlet secondary valve orifice 95b', a third outlet primary valve orifice C3' is connected to a third outlet secondary valve orifice 95c' and a fourth outlet primary valve orifice C4' is connected to a fourth outlet secondary valve orifice 95d', in a second rotor position: the first inlet primary valve orifice C1 is connected to the fourth inlet secondary valve orifice 95d, the second inlet primary valve orifice C2 is connected to the first inlet secondary valve orifice 95a, the third inlet primary valve orifice C3 is connected to the second inlet secondary valve orifice 95b, the fourth inlet primary valve orifice C4 is connected to the third inlet secondary valve orifice 95c, the first outlet primary valve orifice C1' is connected to the fourth outlet secondary valve orifice 95d', the second outlet primary valve orifice C2' is connected to the first outlet secondary valve orifice 95a', the third outlet primary valve orifice C3' is connected to the second outlet secondary valve orifice 95b' and the fourth outlet primary valve orifice C4' is connected to the third outlet secondary valve orifice 95c', in a third rotor position: the first inlet primary valve orifice C1 is connected to the third inlet secondary valve orifice 95c, the second inlet primary valve orifice C2 is connected to the fourth inlet secondary valve orifice 95d, the third inlet primary valve orifice C3 is connected to the first inlet secondary valve orifice 95a, the fourth inlet primary valve orifice C4 is connected to the second inlet secondary valve orifice 95b, the first outlet primary valve orifice C1' is connected to the third outlet secondary valve orifice 95c', the second outlet primary valve orifice C2' is connected to the fourth outlet secondary valve orifice 95d', the third outlet primary valve orifice C3' is connected to the first outlet secondary valve orifice 95a' and the fourth outlet primary valve orifice C4' is connected to the second outlet secondary valve orifice 95b', in a fourth rotor position: the first inlet primary valve orifice C1 is connected to the second inlet secondary valve orifice 95b, the second inlet primary connection C2 is connected to the third inlet secondary valve orifice 95c, the third inlet primary valve orifice C3 is connected to the fourth inlet secondary valve orifice 95d, the fourth inlet primary valve orifice C4 is connected to the first inlet secondary valve orifice 95a, the first outlet primary valve orifice C1' is connected to the second outlet secondary valve orifice 95b', the second outlet primary valve orifice C2' is connected to the third outlet secondary valve orifice 95c', the third outlet primary valve orifice C3' is connected to the fourth outlet secondary valve orifice 95b' and the fourth outlet primary valve orifice C4' is connected to the first outlet secondary valve orifice 95a'.

In one embodiment of the invention a channel is drilled inside the rotor for connecting a second inlet secondary valve orifice with a first outlet secondary valve orifice.

In one embodiment of the invention extra primary connection ports and valve orifices are provided in the stator in order to allow column bypass and/or additional set up of columns.

In one embodiment of the chromatography system inlets of said chromatography columns are connected one to each of said inlet primary connection ports of the rotary valve and outlets of said chromatography columns are connected one to each of said outlet primary connection ports and said inflows are connected one to each of said inlet secondary connection ports and said outflows are connected one to each of said outlet secondary connection ports and wherein said rotor interconnection paths are provided such that each of at least three inflows can be connected one at the time with each of at least three column inlets through the rotary valve and each of at least three outflows can be connected one at the time with each of at least three column outlets through the rotary valve and by rotating the rotor the inflows to the column inlets and the outflows to the column outlets will be shifted according to a simulated moving bed process.

In one embodiment of the chromatography system the feed recirculation flow path comprises a detector. Hereby the number of detectors in the system can be decreased compared to traditional simulated moving bed systems.

DETAILED DESCRIPTION OF EMBODIMENTS OF THE INVENTION

Figure 1:
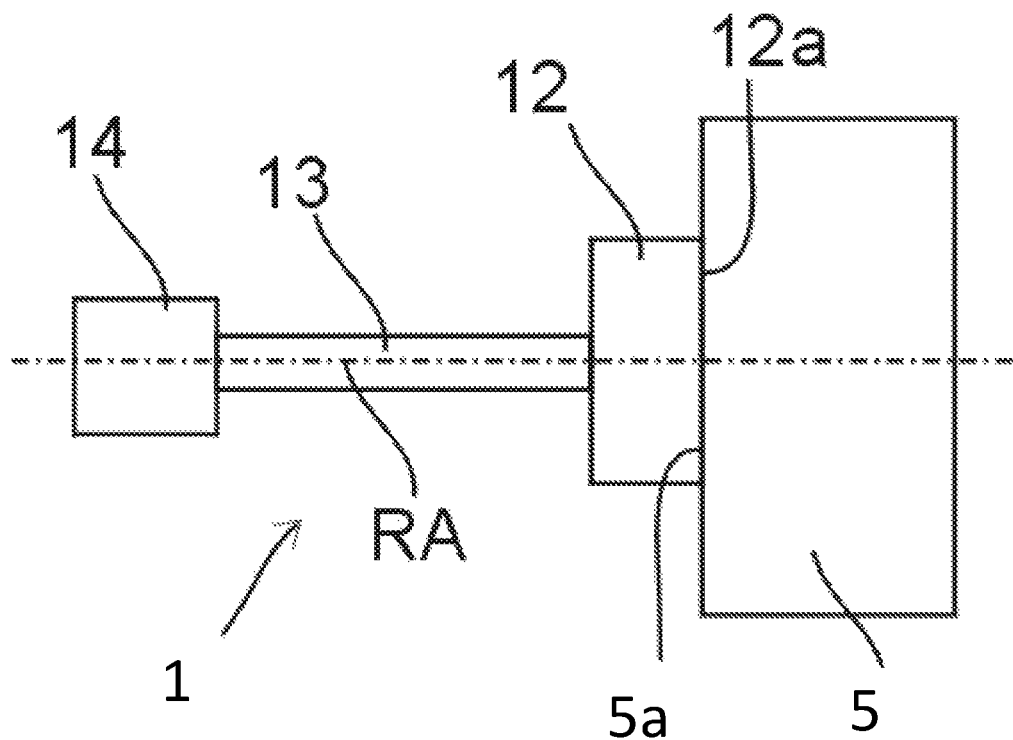
FIG. 1 is a schematic side view of a rotary valve according to one embodiment of the present invention.

The main parts of a typical rotary valve 1 are schematically shown in FIG. 1 (wherein no brackets or similar load carrying or fastening elements are shown). The rotary valve 1 has a stator 5, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 5, which is fixed with respect to the instrument into which it is built, is provided with ports for fluid communication with a fluid source/outlet and any component with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of valve orifices on an inner stator face 5a, i.e. the surface of the stator that during operation is in contact with the rotor 12.

The rotor 12 is typically formed as a disc and has an inner rotor face 12a that is pressed against the flat inner stator face 5a during operation to achieve sealing contact there between. The inner rotor face 12a is provided with one or more interconnection paths which interconnect different valve orifices of the inner stator face 5a depending on the rotary position of the rotor with respect to the stator. The interconnection paths may be any type of path capable of providing fluidic contact between two valve orifices, and may be comprised of an internal channel with discrete orifices, grooves in the inner rotor face or the like.

Figure 2:
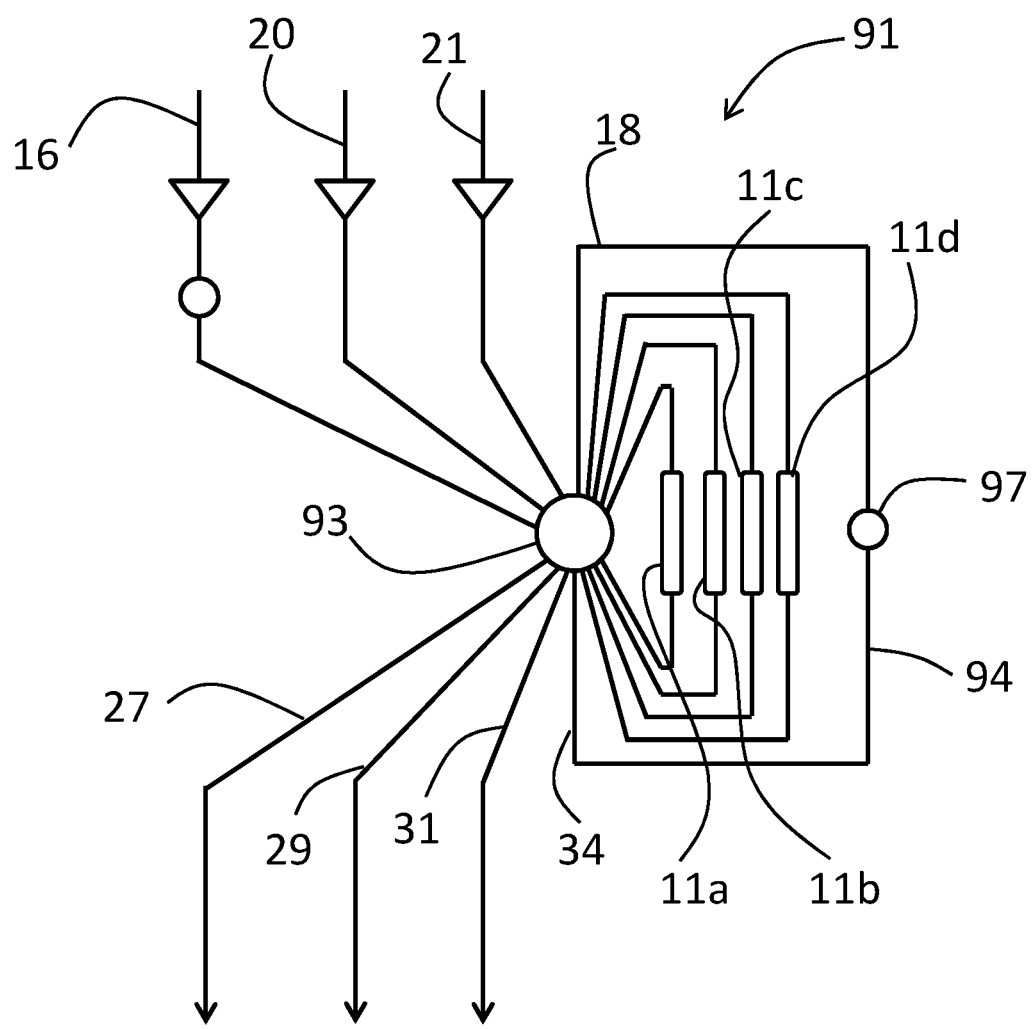
FIG. 2 shows schematically a chromatography system in which a rotary valve according to one embodiment of the invention can be used.

FIG. 2 shows schematically a chromatography system 91 according to one embodiment of the invention. Four columns 11a, b, c, d are shown in this embodiment of the invention. However the rotary valve according to the invention can easily be adopted also for systems with only 3 columns or for systems with more than 4 columns According to the invention only one rotary valve 93 is used for the connection to the columns. This rotary valve 93 is connected to both all the inlets of the four columns and to the outlets. Furthermore it is connected to a first inflow 16, a second inflow 18, a third inflow 20, a fourth inflow 21 and a first outflow 34, a second outflow 27, a third outflow 29 and a fourth outflow 31. In a simulated moving bed chromatography system the first inflow is typically a feed, the second inflow is typically feed recirculation comprising the outflow from the column presently receiving the feed, the third inflow is elution and the fourth inflow is regeneration. The first outflow is typically the feed recirculation, the second outflow is typically feed outlet, the third outflow is typically regeneration outlet and the fourth outflow is typically elution outlet. The rotary valve according to the invention can be used in a simulated moving bed system. According to this embodiment of the invention the rotary valve 93 is connected to a feed recirculation flow path 94 enabling feed recirculation from outlet of a load column in the simulated moving bed system to inlet of a secondary load column in one single feed recirculation flow path 94. The feed recirculation flow path is connected to the rotary valve 93 as a second inflow and as a first outflow. In one embodiment of the invention the feed recirculation flow path 94 also comprises a detector 97. This detector is adapted to detect an effluent signal being representative of the composition of the feed recirculation flowing through the feed recirculation flow path 75. In one embodiment the detector is a UV detector, i.e. measuring the UV absorbance of the sample. Other possible types of detectors are measuring pH, conductivity, light scattering, fluorescence, IR or visible light. This definition of detector will be the same throughout the description.

A schedule for a simulated moving bed method could in one embodiment of the invention be that if the feed is directed to the first column 11a then the outflow from the first column 11a should be directed to the inlet of the second column 11b. The second column 11b hereby serves as a secondary load column and the first column serves as a primary load column. When the first column is fully loaded, which could be measured by for example UV or time, the feed is instead directed directly to the second column 11b (hereby serving as primary load column) and the outflow from the second column 11b is directed to the inlet of the third column 11c, which then serves as the secondary load column. At the same time the first column 11a is eluted by directing the elution buffer (fourth inflow 21) to the inlet of the first column 11a and let the outflow from the first column 11a be directed to the fourth outflow 31 (elution outlet). When the feed is directed directly to the third column 11c the second column is eluted and the first column is at the same time regenerated, whereby regeneration buffer is provided by the third inflow 20 to the inlet of the first column 11a and the outflow is directed to the third outflow 29 (regeneration outlet). The last step in the continuous process is that the first column 11a serves as secondary load column when the feed is directed directly to the fourth column 11d. Then the outflow from the first column 11a is directed to the feed outlet through the second outflow 27. This is a known process for simulated moving bed techniques, also called periodic counter current. The benefit with a feed recirculation is that the risk of losing any possible unbound feed is decreased and therefore the amount of sample provided to the column in the feed can be much higher than in normal chromatography. If there is any unbound feed left in the feed liquid after having passed the primary load column it will have another chance to bind in the secondary load column. This process is recycled. The rotary valve 93 is controlled from a control system such that these above described flows are provided.

Figure 3:
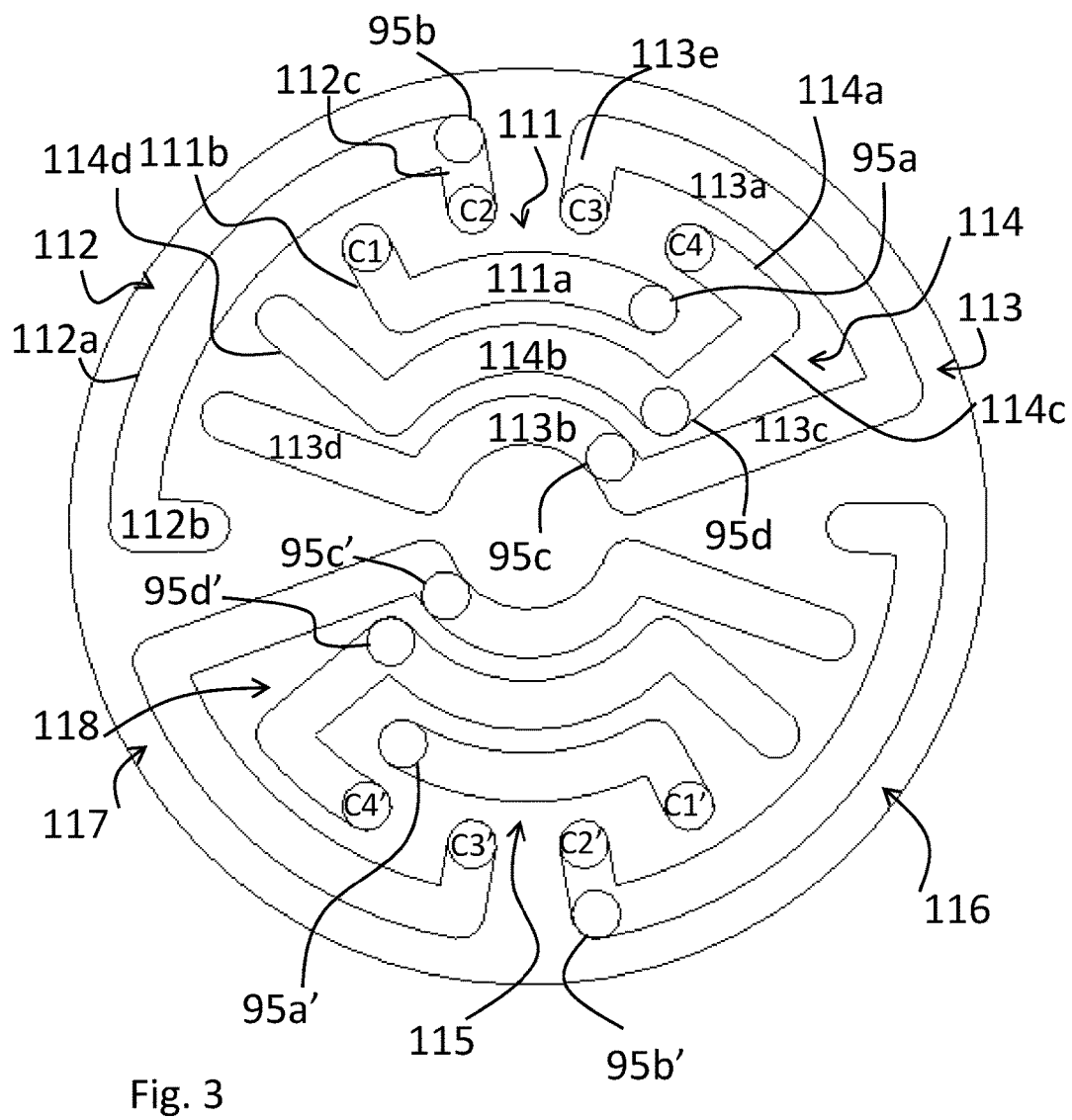
FIG. 3 shows a rotary valve according to one embodiment of the invention that can be used in the chromatography system of FIG. 2.
Figure 4A:
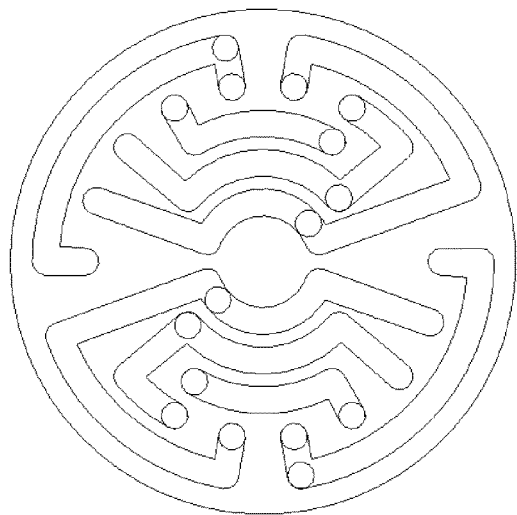
FIGS. 4a, b, c, d show the four different rotor positions of the rotary valve shown in FIG. 3.
Figure 4B:
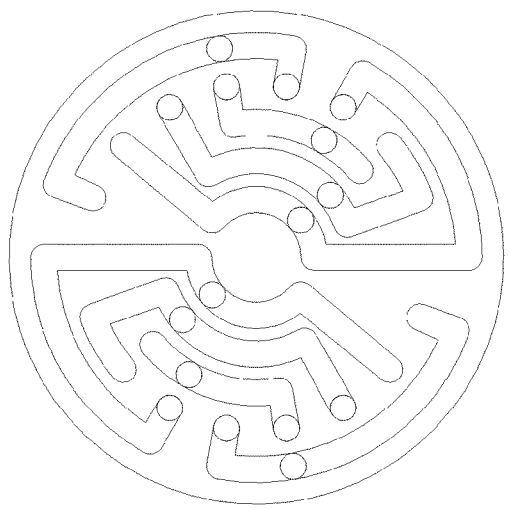
Figure 4C:
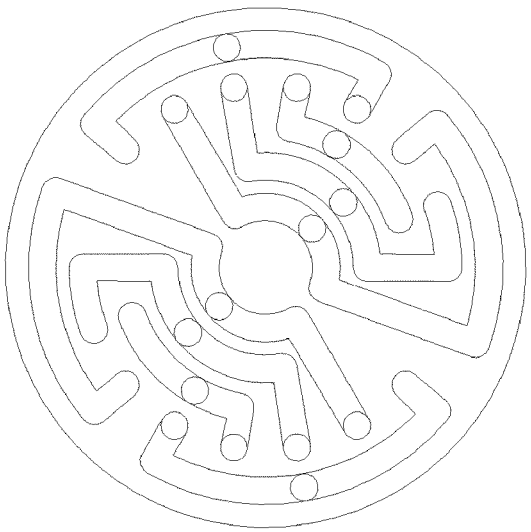
Figure 4D:
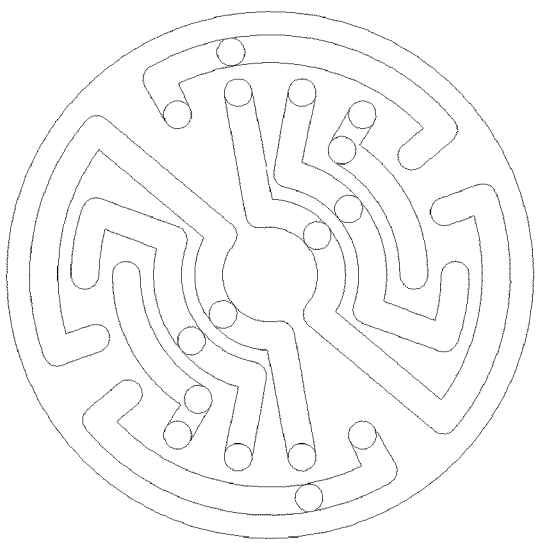

FIG. 3 shows the design of a rotary valve that can be used in the embodiment of the invention shown in FIG. 2. The inlet functions have been provided on one side of the rotor and stator (upper half in FIG. 3) and the outlet functions on the other side. A rotary valve comprises a stator with an inner stator face, and a rotor with an inner rotor face arranged in sealing contact with the inner stator face. The rotor is rotatably movable to a plurality of rotor positions about a rotational axis relative to the inner stator face. The stator comprises a plurality of connection ports each being in fluidic contact with a corresponding valve orifice at the inner stator face and the rotor comprises two or more interconnection paths for selective fluidic interconnection of said valve orifices with respect to the rotor position. In FIG. 3 the valve orifices on the inner stator face and the interconnecting paths on the rotor are shown in the same view. In this embodiment of the rotary valve used in FIG. 2 the stator comprises four inlet primary valve orifices C1, C2, C3, C4 each being in fluidic contact with a corresponding inlet primary connection port of the stator. These inlet primary connection ports are in this example connected to the inlets of the four columns in FIG. 2. The stator comprises further four outlet primary valve orifices C1', C2', C3', C4' each being in fluidic contact with a corresponding outlet primary connection port of the stator. These outlet primary connection ports are in this example connected to the outlets of the four columns in FIG. 2. Furthermore the stator comprises four inlet secondary valve orifices 95a, 95b, 95c, 95d each being in fluidic contact with a corresponding inlet secondary connection port of the stator. These inlet secondary connection ports are in this example connected to the four inflows 16, 18, 20, 21 of FIG. 2. The stator comprises further four outlet secondary valve orifices 95a', 95b', 95c', 95d' each being in fluidic contact with a corresponding outlet secondary connection port of the stator. These outlet secondary connection ports are in this example connected to the four outflows 34, 27, 29, 31 of FIG. 2. The interconnection paths in the rotor are arranged to: in the different rotor positions interconnect the inlet primary valve orifices C1, C2, C3, C4 with the inlet secondary valve orifices 95a, 95b, 95c, 95d and the outlet primary valve orifices C1', C2', C3', C4' with the outlet secondary valve orifices 95a', 95b', 95c', 95d' such that all inlet secondary valve orifices can be connected one at the time to each inlet primary valve orifice and all outlet secondary valve orifices can be connected one at the time to each outlet primary valve orifice by rotating the rotor into the different rotor positions. Hereby all inflows 16, 18, 20, 21 in the chromatography system can be connected one at the time to each column inlet and all outflows 34, 27, 29, 31 can be connected one at the time to each column outlet by rotating the rotor into different rotor positions.

In FIG. 3 stator valve orifices are shown by circles. There are four inlet primary valve orifices denoted C1, C2, C3 and C4 and four outlet primary valve orifices denoted C1', C2', C3', C4'. These are in this embodiment connections to the columns in the system. Furthermore there are four inlet secondary valve orifices, a first inlet secondary valve orifice 95a, a second inlet secondary valve orifice 95b, a third inlet secondary valve orifice 95c and a fourth inlet secondary valve orifice 95d. There are also four outlet secondary valve orifices, a first outlet secondary valve orifice 95a', a second outlet secondary valve orifice 95b', a third outlet secondary valve orifice 95c' and a fourth outlet secondary valve orifice 95d'. The first inlet secondary valve orifice 95a will in the embodiment shown in FIG. 2 be connected to feed, the second inlet secondary valve orifice 95b will be connected to feed recirculation, the third inlet secondary valve orifice 95c will be connected to regeneration and the fourth inlet secondary valve orifice 95d will be connected to elution. The first outlet secondary valve orifice 95a' will be connected to feed recirculation as discussed above, the second outlet secondary valve orifice 95b' will be connected to feed outlet, the third outlet secondary valve orifice 95c' will be connected to regeneration outlet and the fourth outlet secondary valve orifice 95d' will be connected to elution outlet as discussed above.

However the order and organisation and naming of these inlet/outlet primary/secondary valve orifices could be varied as long as the simulated moving bed process is followed from rotation of the rotor of the rotation valve. In the rotor of the rotary valve there are in this embodiment provided rotor interconnection paths as grooves. In this embodiment these rotor interconnection paths are provided partly along parts of circles. The rotor interconnection paths are arranged such that each one of the inlet primary valve orifices C1, C2, C3, C4 is connected to one each of the inlet secondary valve orifices 95a, b, c, d in each rotational position of the rotary valve and such that each one of the outlet primary valve orifices C1', C2', C3', C4' is connected to one each of the outlet secondary valve orifices 95a', 95b', 95c', 95d' in each rotation position of the rotary valve. By rotating the rotor of the rotary valve into four different positions the inflow/outflow connections to the columns will be shifted according to the simulated moving bed process. This is also shown in FIGS. 4a-4d.

Furthermore in this example the rotor will only be rotated over around 60 degrees. The design of the rotor interconnection paths and the position of the stator valve orifices are provided such that a rotation of the rotor at the same time as providing wanted connection shift on the inlet side provides the wanted connection shift on outlet side, i.e. if for example feed is shifted from C1 to C2 the feed recirculation should at the same time on the outlet side shift from C1 to C2 which will be the case if the rotor in FIG. 3 is rotated one step to the right. At the same time the elution buffer (fourth inflow) will be shifted to C1 on inlet side and the elution outlet (fourth outflow) to C1 on outlet side. All the grooves have bended parts and extension parts to achieve this. In more detail the inlet primary valve orifices C1, C2, C3, C4 and the outlet primary valve orifices C1', C2', C3', C4' are all provided along a primary circle 81'. The inlet primary valve orifices are provided on one half of the primary circle 81' (upper part of valve in FIG. 3) and the outlet primary valve orifices are provided on the other half of the circle (lower part of valve in FIG. 3). Four inlet rotor interconnection paths 111, 112, 113, 114 are provided on one side (inlet side, upper part in FIG. 3) of the rotary valve with purpose of connecting the inlet primary valve orifices with the inlet secondary valve orifices and four outlet rotor interconnection paths 115, 116, 117, 118 are provided on the other side of the rotary valve (outlet side, lower part in FIG. 3) with purpose of connecting outlet primary valve orifices with outlet secondary valve orifices. The first inlet rotor interconnection path 111 comprises one first bended part 111a positioned just inside the primary circle 81' and one first extension part 111b connected to the first bended part 111a and reaching out to the primary circle 81'. The first inlet secondary valve orifice 95a is provided in the first bended part 111a. The second inlet rotor interconnection path 112 comprises a second bended part 112a positioned just outside the primary circle 81' and two second extension parts 112b, 112c connected to the second bended part 112a one in each end of the second bended part 112a and both reaching out to the primary circle 81'. The third inlet rotor interconnection path 113 comprises an outer third bended part 113a and an inner third bended part 113b. The outer third bended part 113a is positioned outside the primary circle 81' at the same radial distance as the second bended part 112a but at another part of that circle and the inner third bended part 113b is positioned inside both the primary circle 81' and the first bended part 111a. The third inlet rotor interconnection path 113 comprises further a third connecting part 113c connecting the two third bended parts 113a, 113b and two third extension parts 113d, 113e, one (113d) connected to the inner third bended part 113b and reaching out to the primary circle 81' and one (113e) connected to the outer third bended part 113a and reaching in to the primary circle 81'. The fourth inlet rotor interconnection path 114 comprises one inner fourth bended part 114a and one outer fourth bended part 114b. The inner fourth bended part 114a is positioned on a part of the primary circle 81' and the outer fourth bended part 114b is positioned between the first bended part 111a and the inner third bended part 113b. The fourth inlet rotor interconnection path comprises further a fourth connection part 114c connecting the two fourth bended parts 114a, 114b and a fourth extension part connected with the inner fourth bended part 114b and reaching out to the primary circle 81'. The outlet rotor interconnection paths 115, 116, 117, 118 are designed the same but mirrored on the outlet part of the rotary valve (lower part in FIG. 3).

FIGS. 4a-d show the four different rotor positions:
In a first rotor position the first inlet primary valve orifice C1 is connected to the first inlet secondary valve orifice 95a, the second inlet primary valve orifice C2 is connected to the second inlet secondary valve orifice 95b, the third inlet primary valve orifice C3 is connected to a third inlet secondary valve orifice 95c, the fourth inlet primary valve orifice C4 is connected to the fourth inlet secondary valve orifice 95d, the first outlet primary valve orifice C1' is connected to the first outlet secondary valve orifice 95a', the second outlet primary valve orifice C2' is connected to the second outlet secondary valve orifice 95b', the third outlet primary valve orifice C3' is connected to the third outlet secondary valve orifice 95c' and the fourth outlet primary valve orifice C4' is connected to the fourth outlet secondary valve orifice 95d'.
In a second rotor position the first inlet primary valve orifice C1 is connected to the fourth inlet secondary valve orifice 95d, the second inlet primary valve orifice C2 is connected to the first inlet secondary valve orifice 95a, the third inlet primary valve orifice C3 is connected to the second inlet secondary valve orifice 95b, the fourth inlet primary valve orifice C4 is connected to the third inlet secondary valve orifice 95c, the first outlet primary valve orifice C1' is connected to the fourth outlet secondary valve orifice 95d', the second outlet primary valve orifice C2' is connected to the first outlet secondary valve orifice 95a', the third outlet primary valve orifice C3' is connected to the second outlet secondary valve orifice 95b' and the fourth outlet primary valve orifice C4' is connected to the third outlet secondary valve orifice 95c'.

In a third rotor position the first inlet primary valve orifice C1 is connected to the third inlet secondary valve orifice 95c, the second inlet primary valve orifice C2 is connected to the fourth inlet secondary valve orifice 95d, the third inlet primary valve orifice C3 is connected to the first inlet secondary valve orifice 95a, the fourth inlet primary valve orifice C4 is connected to the second inlet secondary valve orifice 95b, the first outlet primary valve orifice C1' is connected to the third outlet secondary valve orifice 95c', the second outlet primary valve orifice C2' is connected to the fourth outlet secondary valve orifice 95d', the third outlet primary valve orifice C3' is connected to the first outlet secondary valve orifice 95a' and the fourth outlet primary valve orifice C4' is connected to the second outlet secondary valve orifice 95b'.

In a fourth rotor position the first inlet primary valve orifice C1 is connected to the second inlet secondary valve orifice 95b, the second inlet primary connection C2 is connected to the third inlet secondary valve orifice 95c, the third inlet primary valve orifice C3 is connected to the fourth inlet secondary valve orifice 95d, the fourth inlet primary valve orifice C4 is connected to the first inlet secondary valve orifice 95a, the first outlet primary valve orifice C1' is connected to the second outlet secondary valve orifice 95b', the second outlet primary valve orifice C2' is connected to the third outlet secondary valve orifice 95c', the third outlet primary valve orifice C3' is connected to the fourth outlet secondary valve orifice 95b' and the fourth outlet primary valve orifice C4' is connected to the first outlet secondary valve orifice 95a'.

Figure 5:
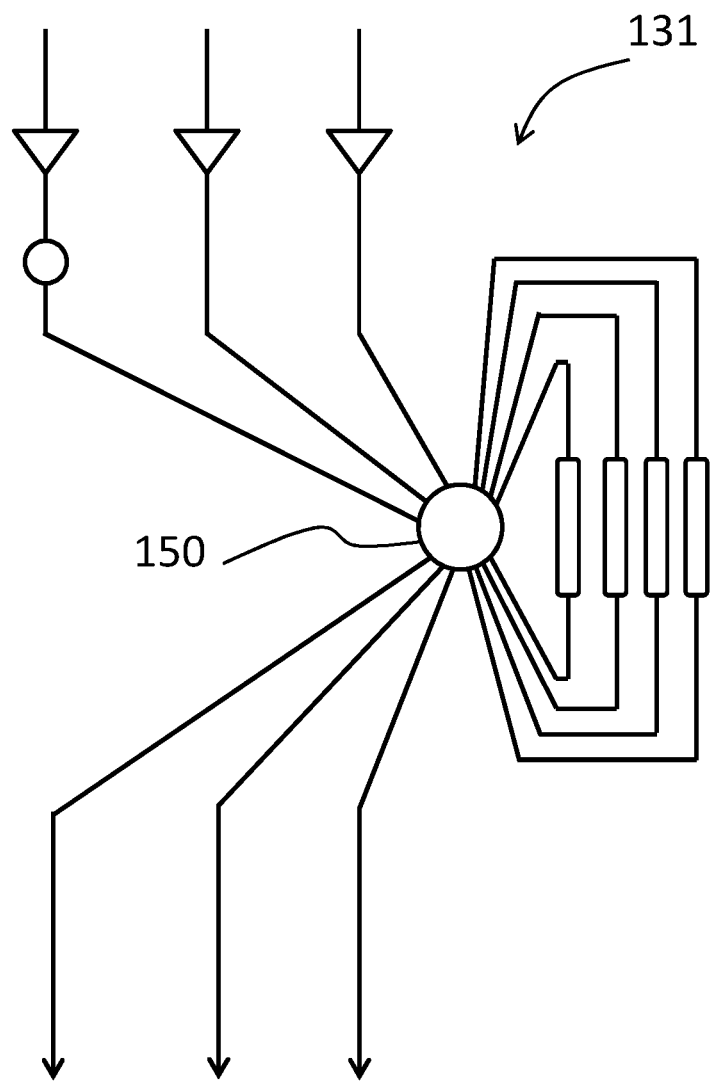
FIG. 5 shows schematically a chromatography system in which a rotary valve according to one embodiment of the invention can be used.
Figure 6:
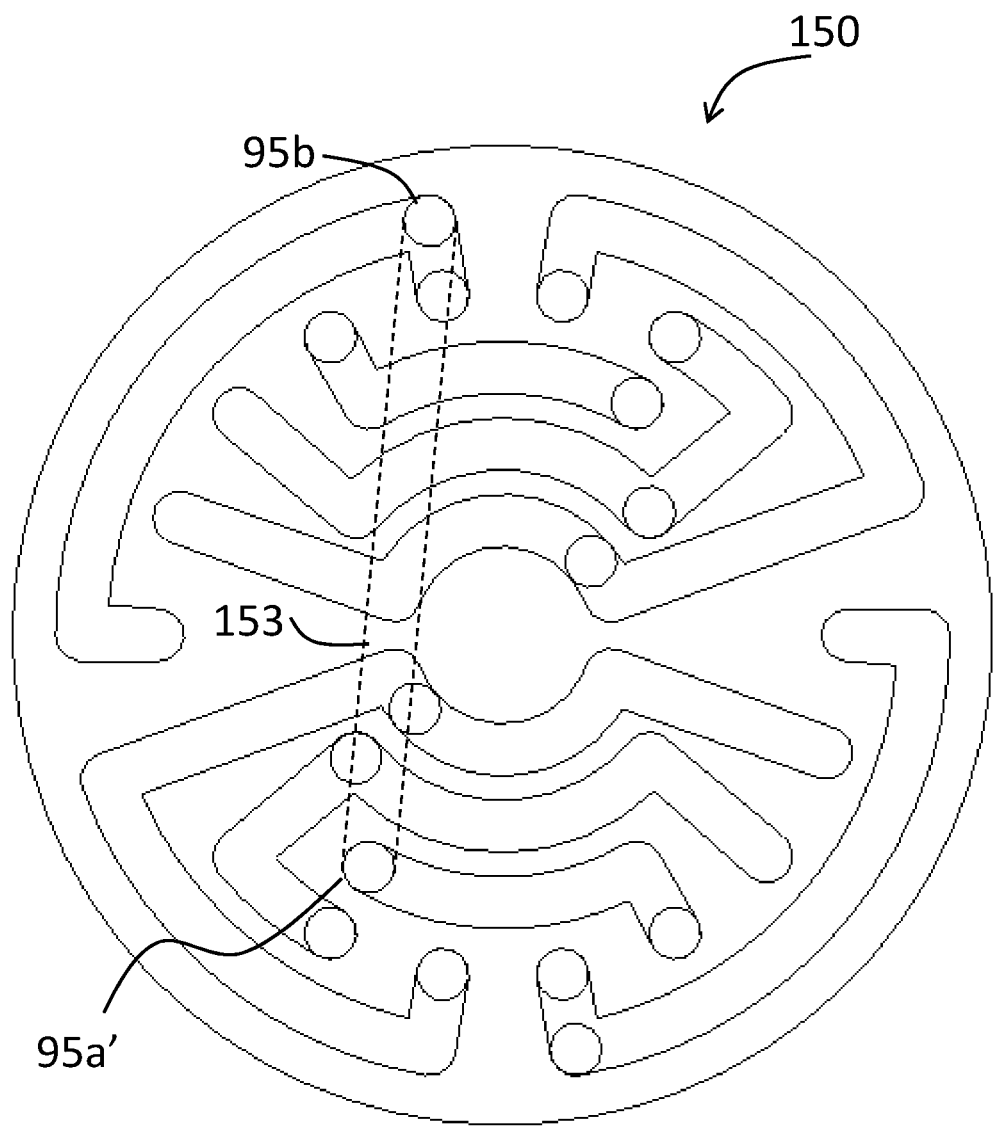
FIG. 6 shows a rotary valve according to one embodiment of the invention that can be used in the chromatography system of FIG. 5.

FIGS. 5 and 6 show schematically a chromatography system 131 and a rotary valve 150 according to one embodiment of the invention. Almost all details are exactly the same as in FIGS. 2 and 3 and will not be described in detail here. The difference is that the feed recirculation path 153 is provided inside the rotary valve 150 itself. It can be a drilled channel within the rotor between the second inlet secondary valve orifice 95b and the first outlet secondary valve orifice 95a'.

Extra column connection ports can be provided in the stator in order to allow column bypass and/or additional set up of columns.

This chromatography system and rotary valve according to the invention can easily be adapted for another number of columns for example three or five columns. Furthermore the rotor interconnection paths can be at least partly provided as drilled channels inside the rotor. This gives more flexibility to the rotor design and less problems with interfering interconnection paths. For example some of the rotor interconnection paths can be composed of one partly circular groove in the rotor surface and one or two drilled radial channels below the rotor surface. The partly circular grooves are then provided concentrically around the centre of the rotor and with different radius and the drilled radial channels are provided as reaching out to the position of the primary valve orifices and connected to one of the circular grooves. One secondary valve orifice is positioned within each one of the circular grooves.

The invention claimed is:

1. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position,
wherein the stator comprises at least three inlet primary connection ports, at least three outlet primary connection ports, at least three inlet secondary connection ports and at least three outlet secondary connection ports, and
wherein the rotor interconnection paths are arranged to:
in the different rotor positions interconnect the inlet primary connection ports with the inlet secondary connection ports and the outlet primary connection ports with the outlet secondary connection ports such that all of at least three inlet secondary connection ports can be connected one at the time to each of at least three inlet primary connection port while simultaneously all of at least three outlet secondary connection ports can be connected one at the time to each of at least three outlet primary connection port by rotating the rotor into the different rotor positions.

2. The rotary valve according to claim 1, wherein by rotating the rotor the interconnections of the primary connection ports with the secondary connection ports will be shifted according to a simulated moving bed process.

3. The rotary valve according to claim 1, wherein the rotor interconnection paths are partly bending grooves.

4. The rotary valve according to claim 1, wherein a channel is drilled inside the rotor for connecting a second inlet secondary valve orifice with a first outlet secondary valve orifice.

5. The rotary valve according to claim 1, wherein extra primary connection ports and valve orifices are provided in the stator in order to allow column bypass and/or additional set up of columns.

6. A chromatography system comprising at least three chromatography columns, said system comprising:
a rotary valve according to claim 1 connected to inlets of at least three columns in the system and to at least three inflows and connected to outlets of at least three columns in the system and to at least three outflows, and
a feed recirculation flow path in which feed recirculation from the outlet of the column presently serving as primary load column in a chromatography process to the inlet of the column presently serving as secondary load column is transferred,
wherein said feed recirculation flow path transfers the feed recirculation from all the columns in the system serving as load columns and wherein said feed recirculation flow path is connected to the inlets and outlets of the columns through the rotary valve.

7. The chromatography system according to claim 6, wherein the inlets of said chromatography columns are connected one to each of said inlet primary connection ports of the rotary valve and the outlets of said chromatography columns are connected one to each of said outlet primary connection ports and said inflows are connected one to each of said inlet secondary connection ports and said outflows are connected one to each of said outlet secondary connection ports and wherein said rotor interconnection paths are provided such that each of the at least three inflows can be connected one at the time with each of the at least three column inlets through the rotary valve and each of the at least three outflows can be connected one at the time with each of the at least three column outlets through the rotary valve and by rotating the rotor the inflows to the column inlets and the outflows to the column outlets will be shifted according to a simulated moving bed process.

8. The chromatography system according to claim 6, wherein the feed recirculation flow path comprises a detector.

9. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position, wherein the stator comprises at least three inlet primary connection ports, at least three outlet primary connection ports, at least three inlet secondary connection ports and at least three outlet secondary connection ports, and wherein the rotor interconnection paths are arranged to:

in the different rotor positions, interconnect the inlet primary connection ports with the inlet secondary connection ports and the outlet primary connection ports with the outlet secondary connection ports such that all of at least three inlet secondary connection ports can be connected one at the time to each of at least three inlet primary connection port while simultaneously all of at least three outlet secondary connection ports can be connected one at the time to each of at least three outlet primary connection port by rotating the rotor into the different rotor positions, wherein the rotor interconnection paths are arranged to:

in a first rotor position: a first inlet primary valve orifice is connected to a first inlet secondary valve orifice, a second inlet primary valve orifice is connected to a second inlet secondary valve orifice, a third inlet primary valve orifice is connected to a third inlet secondary valve orifice, a fourth inlet primary valve orifice is connected to a fourth inlet secondary valve orifice, a first outlet primary valve orifice is connected to a first outlet secondary valve orifice, a second outlet primary valve orifice is connected to a second outlet secondary valve orifice, a third outlet primary valve orifice is connected to a third outlet secondary valve orifice and a fourth outlet primary valve orifice is connected to a fourth outlet secondary valve orifice, in a second rotor position: the first inlet primary valve orifice is connected to the fourth inlet secondary valve orifice, the second inlet primary valve orifice is connected to the first inlet secondary valve orifice, the third inlet primary valve orifice is connected to the second inlet secondary valve orifice, the fourth inlet primary valve orifice is connected to the third inlet secondary valve orifice, the first outlet primary valve orifice is connected to the fourth outlet secondary valve orifice, the second outlet primary valve orifice is connected to the first outlet secondary valve orifice, the third outlet primary valve orifice is connected to the second outlet secondary valve orifice and the fourth outlet primary valve orifice is connected to the third outlet secondary valve orifice, in a third rotor position: the first inlet primary valve orifice is connected to the third inlet secondary valve orifice, the second inlet primary valve orifice is connected to the fourth inlet secondary valve orifice, the third inlet primary valve orifice is connected to the first inlet secondary valve orifice, the fourth inlet primary valve orifice is connected to the second inlet secondary valve orifice, the first outlet primary valve orifice is connected to the third outlet secondary valve orifice, the second outlet primary valve orifice is connected to the fourth outlet secondary valve orifice, the third outlet primary valve orifice is connected to the first outlet secondary valve orifice and the fourth outlet primary valve orifice is connected to the second outlet secondary valve orifice, in a fourth rotor position: the first inlet primary valve orifice is connected to the second inlet secondary valve orifice, the second inlet primary connection is connected to the third inlet secondary valve orifice, the third inlet primary valve orifice is connected to the fourth inlet secondary valve orifice, the fourth inlet primary valve orifice is connected to the first inlet secondary valve orifice, the first outlet primary valve orifice is connected to the second outlet secondary valve orifice, the second outlet primary valve orifice is connected to the third outlet secondary valve orifice, the third outlet primary valve orifice is connected to the fourth outlet secondary valve orifice and the fourth outlet primary valve orifice is connected to the first outlet secondary valve orifice.

10. The rotary valve according to claim 9, wherein by rotating the rotor the interconnections of the primary connection ports with the secondary connection ports will be shifted according to a simulated moving bed process.

11. The rotary valve according to claim 9, wherein the rotor interconnection paths are partly bending grooves.

12. The rotary valve according to claim 9, wherein a channel is drilled inside the rotor for connecting the second inlet secondary valve orifice with the first outlet secondary valve orifice.

13. The rotary valve according to claim 9, wherein extra primary connection ports and valve orifices are provided in the stator in order to allow column bypass and/or additional set up of columns.

14. A chromatography system comprising at least three chromatography columns, said system comprising:

a rotary valve according to claim 9 connected to inlets of at least three columns in the system and to at least three inflows and connected to outlets of at least three columns in the system and to at least three outflows, and a feed recirculation flow path in which feed recirculation from the outlet of the column presently serving as primary load column in a chromatography process to the inlet of the column presently serving as secondary load column is transferred, wherein said feed recirculation flow path transfers the feed recirculation from all the columns in the system serving as load columns and wherein said feed recirculation flow path is connected to the inlets and outlets of the columns through the rotary valve.

15. The chromatography system according to claim 14, wherein the inlets of said chromatography columns are connected one to each of said inlet primary connection ports of the rotary valve and the outlets of said chromatography columns are connected one to each of said outlet primary connection ports and said inflows are connected one to each of said inlet secondary connection ports and said outflows are connected one to each of said outlet secondary connection ports and wherein said rotor interconnection paths are provided such that each of the at least three inflows can be connected one at the time with each of the at least three column inlets through the rotary valve and each of the at least three outflows can be connected one at the time with each of the at least three column outlets through the rotary valve and by rotating the rotor the inflows to the column inlets and the outflows to the column outlets will be shifted according to a simulated moving bed process.

16. The chromatography system according to claim 14, wherein the feed recirculation flow path comprises a detector.

17. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position,
   wherein the stator comprises at least three inlet primary connection ports, at least three outlet primary connection ports, at least three inlet secondary connection ports and at least three outlet secondary connection ports, and
   wherein the rotor interconnection paths are arranged to:
   in the different rotor positions, interconnect the inlet primary connection ports with the inlet secondary connection ports and the outlet primary connection ports with the outlet secondary connection ports such that all of at least three inlet secondary connection ports can be connected one at the time to each of at least three inlet primary connection port while simultaneously all of at least three outlet secondary connection ports can be connected one at the time to each of at least three outlet primary connection port by rotating the rotor into the different rotor positions, wherein the rotor interconnection paths are arranged to:
   in a first rotor position: a first inlet primary valve orifice is connected to a first inlet secondary valve orifice, a second inlet primary valve orifice is connected to a second inlet secondary valve orifice, a third inlet primary valve orifice is connected to a third inlet secondary valve orifice, a fourth inlet primary valve orifice is connected to a fourth inlet secondary valve orifice, a first outlet primary valve orifice is connected to a first outlet secondary valve orifice, a second outlet primary valve orifice is connected to a second outlet secondary valve orifice, a third outlet primary valve orifice is connected to a third outlet secondary valve orifice and a fourth outlet primary valve orifice is connected to a fourth outlet secondary valve orifice,
   in a second rotor position: the first inlet primary valve orifice is connected to the fourth inlet secondary valve orifice, the second inlet primary valve orifice is connected to the first inlet secondary valve orifice, the third inlet primary valve orifice is connected to the second inlet secondary valve orifice, the fourth inlet primary valve orifice is connected to the third inlet secondary valve orifice, the first outlet primary valve orifice is connected to the fourth outlet secondary valve orifice, the second outlet primary valve orifice is connected to the first outlet secondary valve orifice, the third outlet primary valve orifice is connected to the second outlet secondary valve orifice and the fourth outlet primary valve orifice is connected to the third outlet secondary valve orifice,
   in a third rotor position: the first inlet primary valve orifice is connected to the third inlet secondary valve orifice, the second inlet primary valve orifice is connected to the fourth inlet secondary valve orifice, the third inlet primary valve orifice is connected to the first inlet secondary valve orifice, the fourth inlet primary valve orifice is connected to the second inlet secondary valve orifice, the first outlet primary valve orifice is connected to the third outlet secondary valve orifice, the second outlet primary valve orifice is connected to the fourth outlet secondary valve orifice, the third outlet primary valve orifice is connected to the first outlet secondary valve orifice and the fourth outlet primary valve orifice is connected to the second outlet secondary valve orifice,
   in a fourth rotor position: the first inlet primary valve orifice is connected to the second inlet secondary valve orifice, the second inlet primary connection is connected to the third inlet secondary valve orifice, the third inlet primary valve orifice is connected to the fourth inlet secondary valve orifice, the fourth inlet primary valve orifice is connected to the first inlet secondary valve orifice, the first outlet primary valve orifice is connected to the second outlet secondary valve orifice, the second outlet primary valve orifice is connected to the third outlet secondary valve orifice, the third outlet primary valve orifice is connected to the fourth outlet secondary valve orifice and the fourth outlet primary valve orifice is connected to the first outlet secondary valve orifice,
   wherein the rotor interconnection paths are composed of partly circular grooves in a surface of the rotor that are concentrically around the center of the rotor with different radii with one secondary valve orifice positioned within each one of the partly circular grooves.

18. The rotary valve according to claim 17, wherein a channel is drilled inside the rotor for connecting the second inlet secondary valve orifice with the first outlet secondary valve orifice.

* * * * *